United States Patent
Bailey et al.

(10) Patent No.: US 7,432,393 B2
(45) Date of Patent: Oct. 7, 2008

(54) SILICA SUPPORT, HETEROPOLYACID CATALYST PRODUCED THEREFROM AND ESTER SYNTHESIS USING THE SILICA SUPPORTED HETEROPOLYACID CATALYST

(75) Inventors: Craig Bailey, East Yorkshire (GB); Benjamin Patrick Gracey, East Riding of Yorkshire (GB)

(73) Assignee: BP Chemicals Limited, Middlesex (GB)

( * ) Notice: Subject to any disclaimer, the term of this patent is extended or adjusted under 35 U.S.C. 154(b) by 0 days.

(21) Appl. No.: 11/663,331

(22) PCT Filed: Sep. 8, 2005

(86) PCT No.: PCT/GB2005/003470

§ 371 (c)(1),
(2), (4) Date: Mar. 21, 2007

(87) PCT Pub. No.: WO2006/032843

PCT Pub. Date: Mar. 30, 2006

(65) Prior Publication Data

US 2008/0004466 A1    Jan. 3, 2008

(30) Foreign Application Priority Data

Sep. 22, 2004  (GB) ................... 0421012.6
Dec. 22, 2004  (GB) ................... 0428060.8

(51) Int. Cl.
*C07C 67/02*  (2006.01)
*B01J 21/00*  (2006.01)
(52) U.S. Cl. ....................... 560/265; 502/255
(58) Field of Classification Search ............... None
See application file for complete search history.

(56) References Cited

U.S. PATENT DOCUMENTS

| 4,038,211 A | 7/1977 | Frampton | |
|---|---|---|---|
| 2003/0054945 A1* | 3/2003 | Kadowaki et al. | 502/150 |

FOREIGN PATENT DOCUMENTS

| EP | 0 955 284 A | 11/1999 |
|---|---|---|
| GB | 1 371 905 A | 10/1974 |
| WO | WO 00/45952 | 8/2000 |
| WO | WO 02/20158 A2 | 3/2002 |

\* cited by examiner

*Primary Examiner*—Paul A Zucker
(74) *Attorney, Agent, or Firm*—Nixon & Vanderhye

(57) ABSTRACT

A silica support for use in the manufacture of a silica supported heteropolyacid catalyst for use in producing a carboxylic ester from a monocarboxylic acid, olefin and water wherein the support is produced by treating silica-gel granules with steam at a temperature in the range 100 to 300° C. for a period of time in the range 0.1 to 200 hours.

43 Claims, No Drawings

SILICA SUPPORT, HETEROPOLYACID CATALYST PRODUCED THEREFROM AND ESTER SYNTHESIS USING THE SILICA SUPPORTED HETEROPOLYACID CATALYST

This application is the U.S. National Phase of International Application PCT/GB2005/003470, filed 8 Sep. 2005, which designated the U.S. PCT/GB2005/003470 claims priority to British Application No. 0421012.6 filed 22 Sep. 2004 and British Application No. 0428060.8 filed 22 Dec. 2004. The entire content of these applications are incorporated herein by reference.

The present invention relates to a silica support, a heteropolyacid acid catalyst prepared from the silica support and use of the supported heteropolyacid catalyst in the synthesis of esters of monocarboxylic acids by reacting an olefin with a carboxylic acid and processes for producing the support, catalyst and ester. The support, catalyst and process are particularly well adapted for the production of ethyl acetate by the reaction of ethylene with acetic acid.

It is well known that olefins can be reacted with lower aliphatic carboxylic acids to form the corresponding esters. One such method is described in GB-A-1259390 in which an ethylenically unsaturated compound is contacted with a liquid medium comprising a carboxylic acid and a free heteropolyacid of molybdenum or tungsten. This process is a homogeneous process in which the heteropolyacid catalyst is unsupported. A further process for producing esters is described in JP-A-05294894 in which a lower fatty acid is reacted with a lower olefin to form a lower fatty acid ester, the reaction being carried out in the gaseous phase in the presence of a catalyst consisting of at least one heteropolyacid salt of a metal e.g. Li, Cu, Mg or K, supported on a carrier. The heteropolyacid used is phosphotungstic acid and the carrier described is silica.

EP-A-0757027 (BP Chemicals) discloses a process for the production of lower aliphatic esters, for example ethyl acetate, by reacting a lower olefin with a saturated lower aliphatic carboxylic acid in the vapour phase in the presence of a heteropolyacid catalyst characterised in that an amount of water in the range from 1-10 mole % based on the total of the olefin, aliphatic mono-carboxylic acid and water is added to the reaction mixture during the reaction. The presence of water is said to reduce the amount of unwanted by-products generated by the reaction.

A general problem encountered with the above processes in the production of ethyl acetate using heteropolyacid catalysts is the generation of small amounts of a variety of by-products. These by-products generally have to be removed from the ester product by separation processes such as fractional distillation and solvent extraction. The applicants have found that one such by-product, butan-2-one or methyl ethyl ketone (MEK), is particularly troublesome due to its close boiling point with ethyl acetate and hence the difficulty in removing it via distillation.

WO 02/20158 and WO 02/00589 describe a process for producing an aliphatic carboxylic acid ester from an aliphatic carboxylic acid and an olefin catalysed by a supported heteropolyacid catalyst, wherein the catalyst is contacted with a gas containing one or more of water, a lower aliphatic carboxylic acid or a lower aliphatic alcohol to obtain a catalyst for use in producing a lower aliphatic carboxylic acid ester.

It has now been found that special treatment of the silica used to support the heteropolyacid catalyst used for the production of esters by the reaction of olefins and monocarboxylic acids can result in a significant reduction in the levels of undesirable by-products. It has also been found that the treatment can lead to extended catalyst life, an improvement in the crush strength of the supported catalysts and an improvement in the attrition resistance of the supported catalyst.

It is an object of the present invention to provide an improved process for the production of carboxylic acid esters produced by the reaction of 1-olefins with monocarboxylic acids and water in the presence of heteropolyacid catalyst.

Accordingly, the present invention provides a process for producing a support for use in a supported heteropolyacid acid catalyst for use in the production of an ester by reacting a 1-olefin with a monocarboxylic acid and water in the vapour phase wherein the process comprises treating silica-gel granules with steam at a temperature in the range 100 to 300° C. for a period of time in the range 0.1 to 200 hours.

The present invention also provides a support as prepared by the above-mentioned process.

In addition, the present invention provides a process for producing a silica-gel supported heteropolyacid catalyst for use in the production of an ester by reacting a 1-olefin with a monocarboxylic acid and water in the vapour phase wherein the catalyst is produced by impregnating and/or depositing at least one heteropolyacid onto a support of the present invention.

Furthermore, the present invention provides a silica-gel supported heteropolyacid catalyast as prepared by the process as mentioned above.

Yet further, the present invention provides a process for the production of an ester by reacting a 1-olefin with a monocarboxylic acid and water in the vapour phase in the presence of a silica gel-supported heteropolyacid catalyst, wherein the silica gel support is in the form of granules, the granules having been subjected to treatment with steam at a temperature in the range 100 to 300° C. for a period of time in the range 0.1 to 200 hours.

Suitable types of silica gel can be manufactured, for example, by the hydrolysis of $SiCl_4$ with water or by acidifying aqueous silicate solution, for example by the addition of mineral acid to sodium silicate solution. Preferably the support has an average particle diameter of 2 to 10 mm, more preferably 2.5 to 8 mm, and especially 3 to 6 mm.

The granules of the support can be fragments, for example formed by drying the silica gel or by crushing and sieving dried silica gel masses or by pellitisation or extrusion of silica to form regular or irregular particles. The granules can be spheroidal, tubular, cylindrical or any other suitable shapes.

Examples of commercially available silica supports that can be employed in the process of the present invention are Grace 57 granular and Grace SMR 0-57-015 grades of extruded silica. Grace 57 silica has an average pore volume of about 1.15 ml/g and an average particle size ranging from about 3.0-6.0 mm.

The silica gel granules used as support suitably have a pore volume in the range from 0.3-1.8 ml/g, preferably from 0.6-1.2 ml/g and a single pellet crush strength of at least 7 Newtons force. The crush strengths quoted are based on average of that determined for each set of 50 particles on a CHATTILLON tester which measures the minimum force necessary to crush a particle between parallel plates. The support suitably has an average pore radius (prior to supporting the catalyst thereon) of 10 to 500 Å preferably an average pore radius of 30 to 250 Å.

In order to achieve optimum performance, the support is suitably free from extraneous metals or elements which can adversely affect the catalytic activity of the system. If silica is employed as the sole support material it preferably has a purity of at least 99% w/w, i.e. the impurities are less than 1% w/w, preferably less than 0.60% w/w and more preferably less than 0.30% w/w.

The treatment of the silica gel support with steam is carried out before the heteropolyacid catalyst is applied to the support or is carried out simultaneously with the application of the heteropolyacid to the support. The steam treatment is carried out at a temperature in the range 100 to 300° C., preferably 130 to 250° C., more preferably 150 to 200° C. The length of time the silica gel is subjected to the steam treatment is in the range 0.1 to 200, preferably 0.1 to 100, more preferably 0.1 to 70 hours. The steam can be pure steam if desired, or can be a mixture of steam with other gaseous or volatile components, for example air or nitrogen. The partial pressure of the water can vary from 1 to 100% of the total pressure. The total pressure suitably lies in the range 0.1 to 50 barg, preferably 0.1 to 10 barg, more preferably 1 to 8 barg, most preferably 1 to 5 barg.

The silica gel granules can be subjected to treatment with steam using any suitable commercial equipment. For example the granules can be placed in a fixed bed or moving bed and the steam passed in or over the bed for the desired period of time. A fluidised bed of the granules can also be employed, but this can lead to undesirable attrition of the granules. Preferably the granules are placed on trays in an insulated autoclave and the steam is passed in at the desired pressure and temperature.

At completion of the steam treatment, the support can be dried if desired. For example, the support can be dried using a stream of dry air or nitrogen.

The heteropolyacid is loaded on to the support subsequent to or during the steam treatment. The heteropolyacid is loaded on to the support using conventional methods. The product is then ready for use as catalyst for the addition reaction of olefin to carboxylic acid.

The term "heteropolyacid" as used herein and throughout the specification is meant to include the free acids and/or metal salts thereof. The heteropolyacids used to prepare the esterification catalysts of the present invention therefore include inter alia the free acids and co-ordination type salts thereof in which the anion is a complex, high molecular weight entity. The heteropolyacid anion comprises from two to eighteen oxygen-linked polyvalent metal atoms, which are generally known as the "peripheral" atoms. These peripheral atoms surround one or more central atoms in a symmetrical manner. The peripheral atoms are usually one or more of molybdenum, tungsten, vanadium, niobium, tantalum and other metals. The central atoms are usually silicon or phosphorus but can comprise any one of a large variety of atoms from Groups I-VIII in the Periodic Table of elements. These include, for instance, cupric ions; divalent beryllium, zinc, cobalt or nickel ions; trivalent boron, aluminium, gallium, iron, cerium, arsenic, antimony, phosphorus, bismuth, chromium or rhodium ions; tetravalent silicon, germanium, tin, titanium, zirconium, vanadium, sulphur, tellurium, manganese nickel, platinum, thorium, hafnium, cerium ions and other rare earth ions; pentavalent phosphorus, arsenic, vanadium, antimony ions; hexavalent tellurium ions; and heptavalent iodine ions. Such heteropolyacids are also known as "polyoxoanions", "polyoxometallates" or "metal oxide clusters".

Heteropolyacids usually have a high molecular weight e.g. in the range from 700-8500 and include dimeric complexes. They have a relatively high solubility in polar solvents such as water or other oxygenated solvents, especially if they are free acids and in the case of several salts. The solubility can be controlled by choosing the appropriate counter-ions. Specific examples of heteropolyacids and their salts that may be used as the catalysts in the present invention include:

12-tungstophosphoric acid—$H_3[PW_{12}O_{40}].xH_2O$ 12-molybdophosphoric acid—$H_3[PMo_{12}O_{40}].xH_2O$ 12-tungstosilicic acid—$H_4[SiW_{12}O_{40}].xH_2O$ 12-molybdosilicic acid—$H_4[SiMo_{12}O_{40}].xH_2O$ Cesium hydrogen tungstosilicate—$Cs_3H[SiW_{12}O_{40}].xH_2O$ Potassium tungstophosphate—$K_6[P_2W_{18}O_{62}].xH_2O$ Ammonium molybdodiphosphate—$(NH_4)_6[P_2Mo_{18}O_{62}].xH_2O$ Preferred heteropolyacid catalysts for use in the present invention are tungstosilicic acid and tungstophosphoric acid. Particularly preferred are the Keggin or Wells-Dawson or Anderson-Evans-Perloff primary structures of tungstosilicic acid and tungstophosphoric acid.

The impregnated support can be prepared by dissolving the heteropolyacid, in e.g. distilled or demineralised water, and then adding the aqueous solution so formed to the support. The support is suitably left to soak in the acid solution for a duration of several hours, with periodic manual stirring, after which time it is suitably filtered using a Buchner funnel in order to remove any excess acid.

The wet catalyst thus formed is then suitably placed in an oven at elevated temperature for several hours to dry, after which time it is allowed to cool to ambient temperature in a desiccator.

Alternatively, the support may be impregnated with the catalyst by spraying a solution of the heteropolyacid on to the support with simultaneous or subsequent drying (eg in a rotary evaporator).

This supported catalyst can then be used in the addition reaction between the olefin and the monocarboxylic acid. The amount of heteropolyacid deposited/impregnated on the support for use in the esterification reaction is suitably in the range from 10 to 60% by weight, preferably from 30 to 50% by weight based on the total weight of the heteropolyacid and the support.

The acid loading of the catalyst, in g/litre, can be determined by subtracting the weight of the support used from the weight of the catalyst on drying, and then dividing the result by the volume of catalyst support used. For example, if 10 g of catalyst support with a bulk density of 0.40 kg/litre is used in the catalyst preparation, this equates to a catalyst support volume of 0.025 litres. If the weight of dried catalyst prepared from this support is 13.75 g then the total acid loading of the catalyst sample is $(13.75-10)/0.025=150$ g/litre. Acid loadings of the catalyst are also routinely expressed in % wt/wt units. In the above example, an acid loading of 150 g/litre equates to $(3.75/13.75)*100=27.3\%$wt/wt.

In the addition reaction, the olefin reactant used is preferably ethylene, propylene or mixtures thereof. Where a mixture of olefins is used, the resultant product will be inevitably a mixture of esters. The source of the olefin reactant used may be a refinery product or a chemical or a polymer grade olefin which may contain some alkanes admixed therewith. Most preferably the olefin is ethylene.

The mono-carboxylic acid is suitably a $C_1$-$C_4$ carboxylic acid and is preferably a saturated, lower aliphatic mono-carboxylic acid. Acetic acid is preferred.

The reaction mixture suitably comprises a molar excess of the olefin reactant with respect to the aliphatic mono-carboxylic acid reactant. Thus the mole ratio of olefin to the lower carboxylic acid in the reaction mixture is suitably in the range from 1:1 to 15:1, preferably from 10:1 to 14:1.

Preferably the reactants fed or recycled to the reactor contain less than 1 ppm, most preferably less than 0.1 ppm of metals, or metallic compound or basic nitrogen (eg ammonia or amine) impurities. Such impurities can build up in the catalyst and cause deactivation thereof.

The reaction is carried out in the vapour phase suitably above the dew point of the reactor contents comprising the reactant acid, any alcohol formed in situ, and the produced ester. The meaning of the term "dew point" is well known in the art, and is essentially, the highest temperature for a given composition, at a given pressure, at which liquid can still exist in the mixture. The dew point of any vaporous sample will thus depend upon its composition.

Water is present in the reaction mixture. The amount of water can be, for example, in the range from 1 to 15 mole %, preferably from 3 to 12 mole %, more preferably from 5 to 11 mole % based on the total amount of olefin, carboxylic acid and water.

The supported heteropolyacid catalyst is suitably used as a fixed bed which may be in the form of a packed column, or radial bed or a similar commercially available reactor design. The vapours of the reactant olefins and acids are passed over the catalyst suitably at a GHSV (Gas Hourly Space Velocity) in the range from 100 to 5000 per hour, preferably from 300 to 2000 per hour.

The reaction is suitably carried out at a temperature in the range from 150-200° C. The reaction pressure is in the range 5 to 20 barg, preferably from 11 to 15 barg.

The water added to the reaction mixture is suitably present in the form of steam and is capable of generating a mixture of ester and alcohol in the process. The products of the reaction are recovered by e.g. fractional distillation.

EXAMPLE

Two samples of silica were used. The first silica sample was commercially available Grace G57 silica with a 3-6 mm particle diameter. The second silica sample was produced through the hydrothermal treatment of Grace G57 silica using the following method:

25 grams of the silica granules, supported on a glass wool plug, were placed in a 1.5 inch diameter multipurpose microreactor. A preheat bed consisting of 50 ml of carborundum (RTM) silicon carbide granules (mean particle size approximately 1-2 mm) was also installed on top of the silica gel, separated from the silica by a second glass wool plug. The use of a preheat bed within the heated microreactor allows any liquid feed to fully vaporize prior to contacting the silica catalyst support.

Hydrothermal modification of the silica was then carried out by feeding a mixture of 21.6 g/hr of nitrogen and 6 g/hr of steam through the reactor at 13 barg, and 210° C. for a period of 20 hours. Following this, the steam flow was switched off and the reactor was allowed to cool back to ambient under the nitrogen flow only.

The microreactor used in this experiment can be heated from ambient to 300° C. by the use of three independently controlled band heaters. In addition, the pressure in the reactor can be controlled between 0 and 15 barg through the use of a back-pressure regulator. Various gases can be passed through the microreactor from cylinder supplies with the flow controlled with mass flow controllers. Additionally liquid feeds can also be passed through the reactor, these being delivered by an HPLC pump (a "High Pressure Liquid Chromatography" pump designed to deliver very low flows of liquid at very high pressures).

Both samples of silica (the hydrothermally treated and the untreated) were then impregnated with silicotungstic acid by the following method:

Silicotungstic acid hydrate (98 g of 30% solution, Contract Chemicals) was diluted with distilled water to make 100 ml of solution. A 2.5 gram (6.25 ml) sample of either treated or untreated silica was added slowly to this solution and the resulting mixture was then left to stand for 24 hours in a covered beaker with occasional stirring. After 24 hours had elapsed, the silica granules were then filtered to remove any unabsorbed acid solution. The filtered silica was then dried overnight on a ceramic dish at 120° C. The dried silica was then weighed, and the silicotungstic acid uptake (loading) of the silica calculated as previously described:

|  | Untreated G57 Silica gel | Hydrothermally treated G57 Silica gel |
| --- | --- | --- |
| LOADING (grams of silicotungstic acid per litre of silica) | 140 | 134 |

Both catalysts were tested for activity in relation to the production of ethyl acetate and selectivity to methyl ethyl ketone. This was done using a microreactor under the following set of standard screening conditions:

6.25 ml of catalyst (crushed to 0.5-1 mm particle size) was mixed with 6.25 ml of G57 silica of the same particle size and was placed into the microreactor as described above.

The testing conditions used were 185° C. (catalyst temperature), and 11 barg (reactor pressure), with the composition of the gas flowing over the catalyst as follows;

| Component | Feed Rate (g/hr) |
| --- | --- |
| Ethylene | 23.85 |
| Acetic acid | 3.79 |
| Water | 0.99 |
| Diethyl ether | 0.38 |
| s-butanol | 0.05 |

The gas stream from the microreactor was cooled with a heat exchanger and the liquid products collected in a knock out pot and analysed by offline GC (gas chromatography). The remaining gas was analysed by online micro GC.

After 25 hours on stream the productivity of the catalysts were as follows;

|  | Product | |
| --- | --- | --- |
| Catalyst | Ethyl Acetate STY (g/litre cat/hr) | MEK STY (g/litre cat/h) |
| G57 based - not hyrdothermally treated | 485 | 0.0226 |
| Hyrdothermally treated G57 | 489 | 0.0091 |

The catalyst made with the hydrothermally treated catalyst shows approximately the same space time yield (STY) for ethyl acetate as the baseline catalyst. The methyl ethyl ketone production however is significantly reduced.

The invention claimed is:

1. A process for the production of an ester comprising reacting a 1-olefin with a monocarboxylic acid and water in the vapour phase in the presence of a silica gel-supported heteropolyacid catalyst, wherein the silica gel support is in the form of granules, the granules having been subjected to treatment with steam at a temperature in the range 100 to 300°C. for a period of time in the range 0.1 to 200 hours, and wherein the treatment of the support takes place either prior to or simultaneously with the loading of the heteropolyacid onto the support.

2. A process as claimed in claim 1 in which the average particle diameter of the support granules is from 2 to 10 mm.

3. A process as claimed in claim 2 wherein the average particle diameter of the support granules is 2.5 to 8 mm.

4. A process as claimed in claim 3 wherein the average particle diameter is 3 to 6 mm.

5. A process as claimed in claim 1 wherein the silica-gel granules are spheroidal, tubular and/or cylindrical.

6. A process as claimed in claim 1 in which the treatment with steam is at a temperature in the range 130 to 250° C.

7. A process as claimed in claim 6 wherein the temperature is 150 to 200° C.

8. A process as claimed in claim 1 in which the silica purity is at least 99% w/w.

9. A process as claimed in claim 1 in which the support granules have a pore volume in the range from 0.3 to 1.8 ml/g and a single particle average crush strength of at least 7 Newtons force.

10. A process as claimed in claim 9, in which the pore volume is in the range from 0.6 to 1.2 ml/g.

11. A process as claimed in claim 1, in which the average pore radius of the support prior to supporting the catalyst thereon is 10 to 500 Å.

12. A process as claimed in claim 11 wherein the average pore radius is 30 to 250 Å.

13. A process as claimed in claim 1, in which the treatment with steam is carried out at a total pressure of 0.1 to 50 barg.

14. A process as claimed in claim 13 wherein the total pressure is 0.1 to 10 barg.

15. A process as claimed in claim 14 wherein the total pressure is 1 to 5 barg.

16. A process as claimed in claim 1 in which the monocarboxylic acid is a $C_1$ to $C_4$ carboxylic acid.

17. A process as claimed in claim 16 wherein the monocarboxylic acid is acetic acid.

18. A process as claimed in claim 1 in which the 1-olefin is ethylene, propylene or a mixture thereof.

19. A process as claimed in claim 1 in which the heteropolyacid is at least one heteropolyacid selected from the group consisting of tungstophosphoric acid, tungstosilicic acid, molybdosilicic, molybdophosphoric acid and salts thereof.

20. A process as claimed in claim 1 in which the amount of heteropolyacid deposited/impregnated onto the support is in the range from 10 to 60% by weight, based on the total weight of the heteropolyacid and the support.

21. A process as claimed in claim 20 in which the amount of heteropolyacid is from 30 to 50% by weight.

22. A process as claimed in claim 1 wherein water is present in the range 1 to 15 mole % based on the total amount of olefin, monocarboxylic acid and water.

23. A process as claimed in claim 1 wherein the olefin is present in a molar excess with respect to the monocarboxylic acid.

24. A process as claimed in claim 1 wherein the Gas Hourly Space Velocity is in the range from 100 to 5000 per hour.

25. A process as claimed in claim 1 wherein the temperature is in the range 150 to 200° C.

26. A process as claimed in claim 1 wherein the pressure is in the range 5 to 20 barg.

27. A process as claimed in claim 1 wherein the process is carried out as a fixed-bed process.

28. A process for producing a silica-gel supported heteropolyacid catalyst for use in the production of an ester comprising reacting a 1-olefin with a monocarboxylic acid and water in the vapour phase wherein the catalyst is produced by impregnating and/or depositing at least one heteropolyacid onto a support, wherein the support is prepared by treating silica-gel granules with steam at a temperature in the range 100 to 300° C. for a period of time in the range 0.1 to 200 hours, and wherein treating the support takes place either prior to or simultaneously with the loading of the heteropolyacid onto the support.

29. A process according to claim 28 wherein the granules are spheroidal, tubular and/or cylindrical.

30. A process according to claim 28 wherein the silica-gel granules have an average particle diameter in the range 2 to 10 mm.

31. A process as claimed in claim 30 wherein the average particle diameter is in the range 2.5 to 8 mm.

32. A process as claimed in claim 31 wherein the average particle diameter is 3 to 6 mm.

33. A process according to claim 28 wherein the treatment with steam is carried out at a temperature in the range 130 to 250° C.

34. A process as claimed in claim 33 wherein the temperature is 150 to 200° C.

35. A process according to claim 28 wherein the treatment with steam is carried out at a total pressure of 0.1 to 50 barg.

36. A process according to claim 35 wherein the total pressure is 0.1 to 10 barg.

37. A process according to claim 36 wherein the total pressure is 1 to 8 barg.

38. A process according to claim 37 wherein the total pressure is 1 to 5 barg.

39. A process according to claim 28 wherein the support has a pore volume in the range 0.3 to 1.8 ml/g and a single particle crush strength of at least 7 Newtons force.

40. A process according to claim 28 wherein the heteropolyacid is selected from the group consisting of tungstophosphoric acid, tungstosilicic acid, molybdosilicic acid, molybdophosphoric acid and salts thereof.

41. A process according to claim 40 wherein the amount of heteropolyacid deposited/impregnated onto the support is in the range from 10 to 60% by weight, based on the total weight of the heteropolyacid and the support.

42. A process according to claim 41 wherein the amount of heteropolyacid is from 30 to 50% by weight.

43. A silica-gel supported heteropolyacid catalyst for use in the production of an ester by reacting a 1-olefin with a monocarboxylic acid and water in the vapour phase wherein the catalyst is produced according to the process of any one of claims 28 to 42.

* * * * *